United States Patent [19]

Colclough

[11] Patent Number: 5,013,465
[45] Date of Patent: May 7, 1991

[54] DITHIOPHOSPHATES

[75] Inventor: Terence Colclough, Abingdon, England

[73] Assignee: Exxon Chemical Patents, Inc., Linden, N.J.

[21] Appl. No.: 288,292

[22] Filed: Dec. 22, 1988

[30] Foreign Application Priority Data

Dec. 23, 1987 [GB] United Kingdom ............. 8729963

[51] Int. Cl.$^5$ ............................................ C10M 137/04
[52] U.S. Cl. .............................. 252/32.7 E; 558/164; 558/165; 556/18
[58] Field of Search ............... 252/32.7 E; 556/18; 558/164, 165

[56] References Cited

U.S. PATENT DOCUMENTS

| | | | |
|---|---|---|---|
| 2,364,283 | 10/1941 | Freuler | 252/37 |
| 2,364,284 | 6/1941 | Freuler | 252/39 |
| 2,552,570 | 11/1947 | McNab et al. | 252/32.7 |
| 2,618,597 | 2/1951 | McNab et al. | 252/32.7 |
| 2,680,123 | 6/1954 | Mulvany | 260/429 |
| 2,737,492 | 3/1956 | Beegle et al. | 252/32.7 |
| 3,014,940 | 12/1961 | Lynch et al. | 260/429 |
| 3,210,275 | 10/1965 | Durr, Jr. | 252/32.7 |
| 3,288,819 | 11/1966 | Tichelaar et al. | 260/399 |
| 3,290,246 | 12/1966 | Perrotti et al. | 252/32.7 |
| 3,347,790 | 10/1967 | Meinhardt | 252/32.5 |
| 3,401,185 | 9/1968 | Meinhardt | 260/429.9 |
| 3,654,329 | 4/1972 | Imparato et al. | 260/429.9 |
| 3,726,798 | 4/1973 | Silver et al. | 252/75 |
| 4,101,428 | 7/1978 | Crawford | 252/3.27 E |
| 4,253,973 | 3/1981 | Horodysky et al. | 252/46.7 |
| 4,253,978 | 3/1981 | Gemmill et al. | 252/32.7 E |
| 4,255,271 | 3/1981 | Horodysky et al. | 252/46.7 |
| 4,288,335 | 9/1981 | Rivier | 252/32.7 E |
| 4,308,154 | 12/1981 | Clason et al. | 252/32.7 E |
| 4,392,966 | 7/1983 | Schlicht | 252/32.7 E |
| 4,410,434 | 10/1983 | Andress et al. | 252/32.7 R |
| 4,582,920 | 4/1986 | Bridger | 556/25 |
| 4,778,906 | 10/1988 | Love et al. | 556/25 |

FOREIGN PATENT DOCUMENTS 0054804 6/1982 European Pat. Off. .
2056482 3/1981 United Kingdom .

OTHER PUBLICATIONS

Soviet Inventions Illustrated, week 8811, 27th Apr. 1988, section CH: Chemical, Abstract No. 88-075937/11, Derwent Publication Ltd, London GB: & SU-A-1327 972 A (Leningrad Plekhanov Mine) 07-08-1987 (Abstract).
Soviet Inventions Illustrated, week C24, 23rd July 1980, section CH: Chemical, Abstract No. 42806C/24, Derwent Publications Ltd., London, GB: & SU-A-682 526 (Moscow Gubkin Petrochem.) 30-10-1979 (Abstract).

Primary Examiner—Jacqueline V. Howard
Attorney, Agent, or Firm—Jack B. Murray, Jr.; Myron B. Kapustij

[57] ABSTRACT

Metal dithiophosphates obtainable by reacting a basic zinc or copper compound or a molybdenum compound with a dithiophosphoric acid, said dithiophosphoric acid being obtainable by reacting phosphorus pentasulphide with a mixture of alcohols ROH and $R^1(OH)_m$ where m is 1 or 2, the group R is an aliphatic hydrogen- and carbon-containing group having at least 4 carbon atoms, e.g. a $C_4$ to $C_{10}$ alkyl group, or is an alkaryl group, $R^1$ is a hydrogen- and carbon-containing group containing at least 12 carbon atoms and either (a) a

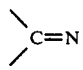

group or (b) the group—$(C_nH_{2n-p}R_p^2O)_q$—, $R^2$ being an alkyl group, n begin an integer of from 2 to 5, p being zero or an integer of from 1 to 5 and q being an integer of 2 or more or $R^1(OH_m$ is a glyceryl derivative having the formula

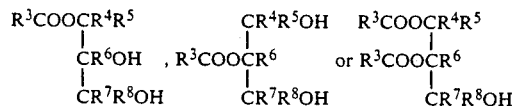

where $R^3$ is an aliphatic hydrogen- and carbon-containing group containing at least 9 carbon atoms and $R^4$, $R^5$, $R^6$ and $R^7$ are hydrogen or alkyl groups. Preferred is the zinc dithiophosphate derived from 2-ethyl hexanol (ROH) and

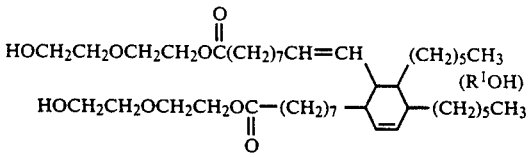

13 Claims, No Drawings

DITHIOPHOSPHATES

This invention relates to dithiophosphates and to lubricating oils containing them.

Zinc dialkyl dithiophosphates (ZDDPs) have been used for many years as antiwear and antioxidant additives in lubricating oils and are typically prepared by reacting a dialkyl dithiophosphoric acid with a basic zinc compound The dialkyl dithiophosphoric acid is usually made by reacting phosphorus pentasulphide with an alcohol In order to increase the surface activity of ZDDPs and hence their antiwear activity, it has been thought possible to prepare ZDDPs from dithiophosphoric acids formed by phosphorus pentasulphide with not the usual $C_4$ to $C_{10}$ alcohol, but an alcohol having a polar group. Patents suggesting this include U.S. Pat. No. 3654329, U.S. Pat. No. 3290246, U.S. Pat. No. 4410434, U.S. Pat. No. 4288335, U.S. Pat. No. 4253973, U.S. Pat. No. 4253978, U.S. Pat. No. 3288819 and U.K. 2031132. However, difficulties have arisen because these ZDDPs made from the alcohols containing a polar group are often oil-insoluble.

ZDDPs are multifunctional additives and act as antioxidants, antiwear agents and bearing corrosion inhibitors. ZDDPs are frequently used in the presence of other additives such as polar hydroxy compounds—hydroxyesters (glyceryl mono oleate) imidazolines, alkylphenol/ethylene oxide condensates (Plexol 305) and the hydroxyester formed by esterification of a dimer acid of linoleic acid and diethylene glycol—which act as friction modifiers, fuel economy additives or rust inhibitors. Due to their polar nature, additives of this type may have poor oil solubility, which can limit the treat levels at which they are used. Also, when these polar additives have been tried in certain packages or blends, compatibility problems have been experienced involving sediment formation during storage and this precludes the use of these additives in specific packages.

These polar hydroxy compound are substituted alcohols which could be reacted with phosphorus pentasulphide and then zinc oxide to form a ZDDP, but such a ZDDP would be a highly viscous liquid, or a solid, with poor handling properties and poor oil solubility. It has now been found that by reacting a mixture of a simple $C_4$–$C_{10}$ alcohol together with a certain more polar substituted alcohol, in appropriate proportions, liquid oil-soluble functionalised or friction-modified ZDDPs with excellent handling properties can be made.

An advantage of the friction-modified ZDDPs is that they overcome the compatibility problems previously associated with friction modifiers when used alone. A further advantage is that the friction-modified ZDDPs provide a potential source of higher levels of friction modifier in a blend than were previously obtained when the polar friction modifiers themselves were used, due to their low oil solubility.

A still further advantage is that the introduction of polar groups into a ZDDP usually provides an improvement in antiwear activity.

Accordingly, this invention provides a metal dithiophosphate obtainable by reacting a basic zinc or copper compound or a molybdenum compound with a dithiiophosphoric acid, said dithiophosphoric acid being obtainable by reacting phosphorus pentasulphide with a mixture of alcohols ROH and $R^1(OH)_m$ where m is 1 or 2. The group R is an aliphatic hydrogen- and carbon-containing group having at least 4 carbon atoms or is an alkaryl group, $R^1$ is a hdyrogen- and carbon-containing group containing at least 12 carbon atoms and either (a)

group or (b) the group $—(C_nH_{hd 2n-p}R_p^2O)_q—$, $R^2$ being an alkyl group, n being an integer of from 2 to 5, p being zero or an interger of from 1 to 5 and q being an integer of 2 or more with the proviso that p is less than 2n. Alternatively $R^1(OH)_m$ is a glyceryl derivative and has the formula

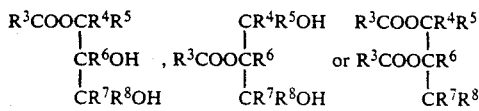

ps where $R^3$ is an aliphatic hydrogen—and carbon-containing group containing at least 9 carbon atoms and $R^4$, $R^5$, $R^6$ and $R^7$ are hydrogen or alkyl groups.

The metal dithiophosphates include those of the formulae

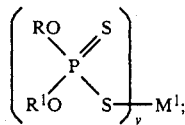

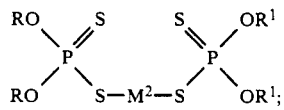

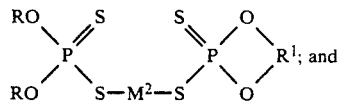

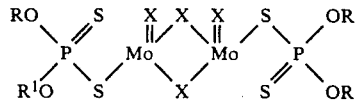

where $M^1$ is cuprous or cupric copper or zinc, $M^2$ is cupric copper or zinc, v being the valency of the metal and X is S or O.

This invention also provides the use of the above defined metal dithiophsophates in a lubricating oil as an antioxidant.

The dithiophosphate is derived from the reaction of the alcohols ROH and $R^1(OH)_m$ with $P_2S_5$. Usually there are four equivalents plus a slight excess of ROH and $R^1(OH)_m$ reacted with $P_2S_5$. Usually there is more of ROH than $R^1(OH)_m$ on a molar basis so as to ensure that a mobile liquid oil-soluble product is formed.

Since the dithiophosphates are prepared by the reaction of $P_2S_5$ with an alcohol the groups R and $R^1$ are derived from the corresponding alcohols ROH and $R^1(OH)_m$.

In the above formulae the group R may be an aliphatic hydrogen- and carbon-containing group having at least 4 carbon atoms, e.g. 4 to 10 carbon atoms. This may for example be an alkenyl group but preferably it is $C_4$ to $C_{10}$ alkyl and may for example be a n-butyl, i- butyl, sec-butyl, amyl, sec-hexyl, n-heptyl, n-octyl, i-octyl or n-decyl. Preferably R is 2-ethyl hexyl. Alternatively R can be an alkaryl group and this is preferably an alkyl phenyl group, especially a $C_7$ to $C_{12}$ alkyl phenyl group, e.g. branched nonyl phenyl or branched dodecyl phenyl. R may be a mixture, i.e. derived from a mixture of alcohols ROH.

$R^1$ is a hydrogen- and carbon-containing group containing at least 12 carbon atoms and may contain a $$\diagdown C=N- \diagup$$

group.

The $$\diagdown C=N- \diagup$$

group is preferably an oxazoline group, i.e.

$$-\underset{\underset{O-}{|}}{C}=N-$$

Preferred oxazolines are prepared by reacting substantially equivalent proportions of a monocarboxylic acid and 2-amino diol or triol. Thus $$R^9COOH + H_2N-\underset{\underset{\underset{OH}{|}}{\underset{CR^{10}R^{11}}{|}}}{\overset{R^{13}}{\overset{|}{C}}}-R^{12} \longrightarrow$$

$$\underset{O-CR^{10}R^{11}}{\overset{R^9-C=N}{\diagdown}}\overset{R^{13}}{\underset{}{\diagup}} + 2H_2O$$

where $R^9$ is alkyl or alkenyl, $R^{10}$ and $R^{11}$ are hydrogen or alkyl and $R^{12}$ and $R^{13}$ are alkyl or hydroxy alkyl provided at least one of them is hydroxyalkyl.

The carboxylic acid $R^9COOH$ may have from 9 to 50 carbon atoms. These acids include decanoic, dodecanoic, tetradecanoic, octadecanoic and eicosanoic acids as well as unsaturated acids such as oleic or linoleic acids.

$R^{10}$ and $R^{11}$ are preferably hydrogen but one of them may for example be a low alkyl such as methyl or ethyl.

When a 2-amino diol is reacted it is preferred that $R^{12}$ be hydrogen or a low alkyl such as methyl or ethyl. $R^{13}$ is then preferably hydroxy-$(C_1-C_{10})$ alkyl, for example, hydroxy-methyl, hydroxy-butyl or hydroxy-octyl. When a 2-amino triol is reacted it is preferred that $R^{12}$ and $R^{13}$ each be hydroxy-$(C_1-C_{10})$ alkyl, e.g. hydroxy-methyl.

A particularly preferred amino-triol is 2-amino-2-(hydroxymethyl)-1,3-propane diol. Thus $$R^9COOH + H_2N-\underset{\underset{CH_2OH}{|}}{\overset{\overset{CH_2OH}{|}}{C}}-CH_2OH \longrightarrow$$

$$\underset{O-CH_2}{\overset{R^9-C=N}{\diagdown}}\overset{CH_2OH}{\underset{CH_2OH}{\diagup}} + 2H_2O$$

In this case $R^1(OH)_m$ is $$\underset{O-CH_2}{\overset{R^9-C=N}{\diagdown}}\overset{CH_2OH}{\underset{CH_2OH}{\diagup}}$$

The reaction between the monocarboxylic acid $R^9COOH$ and the 2-amino diol or triol can be carried out by heating the reactants at from 80° C. to 250° C., preferably from 120° C. to 190° C.

The group $R^1$ may contain the polyalkyleneoxide group —$(C_nH_{2n-p}R_p^2O)_q$— where n, p and q and $R^2$ are as previous defined.

$R^1OH$ may therefore be a polyalkylene oxide derivative of an alcohol, a phenol or a fatty acid.

These compounds are of the general formula $$Y(C_nH_{2n-p}R_p^2O)_qH$$

wherein n is preferably in the range of from 2 to 12. Preferably $R^2$ is a low alkyl, eg methyl as in polyoxy propylene or is hydrogen as in polyoxyethylene —$C_nC_{2n-p}R_p^2$— is an alkylene radical of 2–5 carbon atoms representing the hydrocarbyl portion of the one or more alkylene oxide units incorporated into the molecule. Preferably it is the propylene oxide unit —$CH(CH_3)CH_2O$—, or most preferably, the ethylene oxide unit —$CH_2CH_2O$—.

Y can take various forms and it is preferred that Y is the phenoxy fragment having the formula $$R^{14}-\underset{}{\underset{}{\bigcirc}}-O-$$

wherein $R^{14}$ is an aliphatic hydrocarbyl radical having at least 4 carbon atoms If is an alkyl group, and —$C_nC_{2n-p}R^2$ is —$CH_2CH_2$—, then the compound is an alkyl phenoxy poly(oxyethylene)ethanol $R^{14}$ is preferably a saturated $C_9$ or $C_{12}$ branched alkyl radical derived from tripropylene or tetrapropylene, but it could be a linear alkyl radical. The $R^{14}$ group can be derived from synthetic or natural sources Illustrative $R^{14}$ groups are isooctyl, nonyl, dodecyl, tetradecyl, hexadecyl and octadecyl. $R^{14}$ can be polyisobutenyl or other polymers of olefin monomers of from 2 to 6 carbon atoms, and preferably from 3 to 4 carbon atoms.

Examples of the polyalkoxylated phenoxy compounds are isooctyl phenoxy tetraethoxy ethanol, nonylphenoxy poly(oxyethylene)ethanol, dodecyl phenoxy poly(oxyethylene)ethanol, dodecyl phenoxy poly(oxypropylene)propanol, and hexadecadienyl phenoxy poly(oxyethylene)ethanol.

Alternatively Y can be the fatty acid fragment $R^{14}COO$—and $Y(C_nC_{2n-p}R_p^2O)_qH$ is a polyoxyalkylene fatty acid ester. As another alternative Y is the alcoholic fragment, and $R^{14}CH_2O-$ and $Y(-C_nC_{2n-p}R_p^2O)_qH$ is an alkyl or alkenyl poly(oxyalkylene alkanol. Alkyl poly(oxyalkylene)alkanols and alkenyl poly(oxyalkylene)alkanols include decyl poly(oxyethylene)ethanol, dodecyl poly(oxypropylene)propanol, and octadecenyl poly(oxyethylene)ethanol, all of the general formula, $R^{14}(C_nC_{2n-p}R_p^2O)_q$. Of these, the alkyl poly(oxyethylene)ethanols are the preferred embodiment.

Illustrative poly(oxyalkylene) fatty acid esters which are included within the scope of this invention are of the general formula $R^{14}COO(C_nH_{2n-p}R_p^2O)_qH$ and include poly(oxy- ethylene) stearate poly(oxyethylene)laurate, poly- (oxyethylene)oleate, and poly(oxypropylene)stearate.

The most preferred alkoxylated group $R^1$ is of the formula

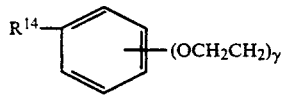

where $R^{14}$ i $C_8$ or $C_9$ alkyl and $\gamma$ is 3 or 4.

Another class of alcohols $R^1(OH)_m$ are hydroxy esters derived from the esterification of a poly-carboxylic acid with a polyglycol Such an ester may be a partial, di- or polyester with typical formulae of the ester represented by the following general formulae when using a polyglycol:

(1) HO—R—OOC—R''—COOH
(2) HO—R—OOC—R''—COOR'—OH
(3) HO—R—OOC—R——COOR—OOC—R'-'—COOR'—OH wherein R'' is the hydrocarbon radical of said acid and each R and R' may be the same or different hydrocarbon radicals associated with the polyglycol as hereinafter defined. It will, of course, be appreciated that esters of the type illustrated by the foregoing formula can be obtained by esterifying a polycarboxylic acid, or a mixture of such acids, with a polyglycol or mixture of such polyglycols.

Suitable carboxylic acids include mono- and polycarboxylic acids. Preferably they are poly-carboxylic acids and they may be aliphatic, saturated or unsaturated and will generally have a total of 24 to 90, preferably 24 to 60 carbon atoms and 2 to 4, preferably 2 or 3 and more preferably 2 carboxylic acid groups with at least 9 up to 42 carbon atoms, preferably 12 to 42 and more preferably 16 to 22 carbon atoms between the carboxylic acid groups.

The oil insoluble polyglycol which is reacted with the polycarboxylic acid such as one of those described above may be a polyalkylene glycol, straight chain or branched. The oxa-alkane diol will, generally, have from 4 to 200, preferably 4 to 100 carbon atoms per molecule. The oxa-alkane diol (polyalkylene glycol) will, of course, contain periodically repeating groups of the formula: $-(-C_nH_{2n-p}R_p^2O)_q$—but the polyalkylene glycol is preferably of the formula

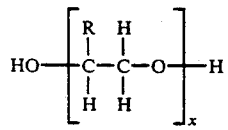

wherein R may be H, $CH_3$, $C_2H_5$ or $C_3H_7$, and x is 2 to 100, preferably 2 to 25. The preferred oxa-alkane diol or polyalkylene glycol is diethylene glycol.

Although any of the esters as set forth above can be effectively used, best results are, however, obtained with such compounds wherein the carboxyl groups of the polycarboxylic acid are separated from each other by from about 16 to about 22 carbon atoms and wherein the hydroxy groups are separated from the closest carboxyl group by from about 2 to about 12 carbon atoms. Particularly desirable results have been obtained with additives prepared by esterifying a dimer of a fatty acid particularly those containing conjugated unsaturation with a polyhydroxy compound Such dimers are clearly taught in U.S. Pat. No. 3,180,832 and U.S. Pat. No. 3,429,817 and as there indicated, the hydrocarbon portion of the dimer or dicarboxylic acid thus obtained may contain a six member ring. The formation of the dimer from linoleic acid, oleic acid and mixtures of these acids is illustrated by the following:

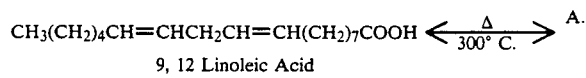

9, 12 Linoleic Acid

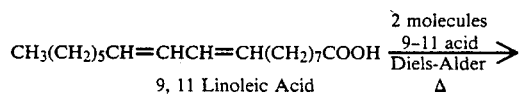

9, 11 Linoleic Acid

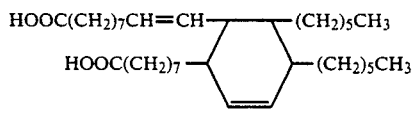

Linoleic Acid Dimer (dilinoleic acid)

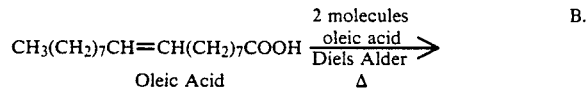

Oleic Acid

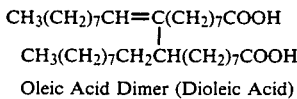

Oleic Acid Dimer (Dioleic Acid)

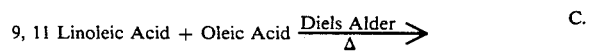

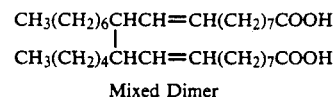

Mixed Dimer

It will, of course, be appreciated that although the reactions illustrated produce the dimers, commercial application of the reactions will, generally, lead to trimer formation and in some cases the product thus obtained will contain minor amounts of unreacted monomer or monomers. As a result, commercially available dimer acids may contain as much as 25% trimer and the use of such mixtures is within the scope of the present invention.

The preferred hydroxy-substituted esters are the reaction product of a dimerized fatty acid, such as those illustrated, and an oil insoluble polyglycol and may be produced by various techniques. As previously pointed out, the preferred acid dimers are the dimers of linoleic acid, oleic acid or the mixed dimer of linoleic and oleic acids, which may also contain some monomer as well as trimer Other specifically satisfactory polyglycols in addition to polyethylene polyglycol are, for example polypropylene glycol, and polybutylene glycol.

Particularly preferred is the hydroxy ester formed by esterification of a dimer acid of linoleic acid and diethylene glycol having the formula

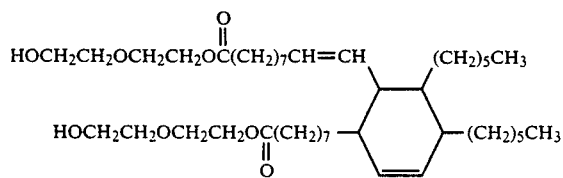

As a third alternative $R^1(OH)_m$ is a glyceryl derivative and has the formula

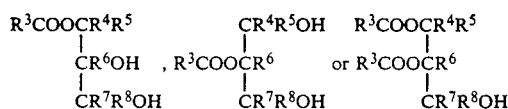

Although $R^4$, $R^5$, $R^6$ and $R^7$ may be alkyl groups they are preferably hydrogen atoms. If alkyl it is preferred that only one or two of them are alkyl and the alkyl group is preferably a $C_1$ to $C_5$ alkyl, for example methyl or ethyl.

$R^3$ is an aliphatic hydrogen- and carbon-containing group and it preferably alkyl or alkenyl. Usually it has 9 to 26 carbon atoms, for example 12 to 22 carbon atoms. Thus it may for example b lauryl, myristyl, palmityl, stearyl, behenyl, oleyl, linoleyl or linolenyl.

Particularly preferred is glyceryl mono oleate i.e.

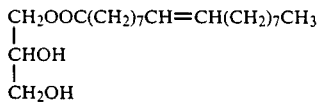

The dithiophosphoric acid from which the dithiophosphate is prepared can be obtained by reacting phosphorus pentasulphide with a mixture of the alcohols ROH and $R^1OH$.

Thus, for a substantially equimolar mixture of alcohols ROH and $R^1OH$:

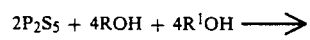

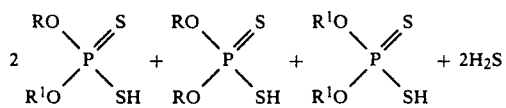

A mixture of acids is thereby obtained and although it would be possible to separate them, e.g. by chromatography, in practice it is not necessary or even particularly desirable to separate them before preparing the metal dithiophosphate. The maximum ratio of $R^1(OH)_m$ to ROH is limited by the need to produce a liquid oil-soluble ZDDP. If $R^1(OH_m/ROH$ is high and gives a viscous liqud ZDDP which is difficult to handle, this can be thinned with diluent oil. The maximum $R^1(OH)_m$./ROH has to be determined by experiment for each case but usually it cannot be more than 50/50 wt. %.

The metal dithiophosphate is obtained by reacting the dithiophosphoric acid with a basic compound of zinc or copper or a molybdenum compound, e.g. molybdic acid or ammonium molybdate. The basic compounds are preferably the oxides, e.g. ZnO, but other salts of the metals can be used provided that the anion can be replaced by the anion of the dithiophosphoric acid. Cuprous oxide is preferred to cupric oxide or cupric hydroxide.

Other basic metal compounds which may be used are preferably soluble in the dithiophosphoric acid. Examples of other suitable basic compounds are the carboxylates, e.g. the stearates, acetates and the carbonates.

When forming the metal dithiophosphate it is often desired to use a promoter. Suitable promoters are carboxylic acids, metal carboxylates and other metal salts, particularly the salts of zinc and ccpper, eg nitrates, phosphates, sulphates or halides. Especially preferred are the zinc salts, particularly zinc carboxylates, zinc chloride, zinc phosphate, zinc nitrate and zinc sulphate. The preferred carboxylic acids for use as such or as their carboxylates are $C_1$ and $C_{20}$ monocarboxvlic acids, eg acetic acid, propionic acid, monocarboxylic acids, eg acetic acid, propionic acid, decanoic acid, stearic acid and oleic acid. The most preferred promoter is zinc acetate.

The amount of promoter used is usually less than 10 weight %, for example between 0.1 and 10 weight % of the total weight of the metal compound.

The metal dithiophosphate is simply prepared by heating together the dithiophosphoric acid with the metal compound and if used, the promoter. The acid may be slowly added to the metal compound which is generally used in the form of a slurry, for example with mineral oil. Alternatively, the metal compound, and promoter if used, are added to about half the acid and then the remainder of the acid added. The reactants are usually heat soaked eg at 40° C. to 60° C. and then heated to a temperature of between 60° C. and 100° C. for example about 85° C. and the remainder of the acid added, if only some acid has been used hitherto. As indicated above the metal compound may be slurried in a liquid vehicle, for example a mineral oil, before reacting with the acid. The amount of vehicle can be quite low, for example 5–10% of the total reaction mixture and it is advantageous to use small amounts because this results in lower treat rates when the metal dithiophosphate is used as a lubricating oil additive.

After maintaining the reactants at the reaction temperature for 1 to 4 hours, eg about 1.0 to 3.0 hours the reaction mixture is preferably cooled, flocculant is added and the mixture is stripped and filtered. The filtrate is the desired product.

The lubricating oil to which the metal dithiophosphate can be added includes mineral lubricating oils and synthetic lubricating oils and mixtures thereof. The synthetic oils include polyalpha olefins, diester oils such as di(2-ethylhexyl) sebacate, azelate and adipate, complex ester oils such as those formed from dicarboxylic acids, glycols and either monobasic acids or monohydric alcohols and silicone oils.

The lubricating oil base stock for the antioxidant additives of the present invention typically is adapted to perform a selected function by the incorporation of additives therein to form lubricating oil compositions (i.e. formulations).

Representative additives typically present in such formulations include viscosity modifiers, corrosion inhibitors, other oxidation inhibitors, other friction modifiers, dispersants, anti-foaming agents, anti-wear agents, pour point depressants, detergents, rust inhibitors and the like.

Viscosity modifiers impart high and low temperature operability to the lubricating oil and permit it to remain shear stable at elevated temperatures and also exhibit acceptable viscosity or fluidity at low temperatures.

Viscosity modifiers are generally high molecular weight hydrocarbon polymers including polyesters The viscosity modifiers may also be derivatized to include other properties or functions, such as the addition of dispersancy properties.

These oil soluble viscosity modifying polymers will generally have number average molecular weights of from $10^3$ to $10^6$, preferably $10^4$ to $10^6$, e.g., 20,000 to 250,000, as determined by gel permeation chromatography or membrane osmometry.

Representative examples of suitable viscosity modifiers are any of the types known to the art including polyisobutylene, copolymers of ethylene and propylene, polymethacrylates, methacrylate copolymers, copolymers of an unsaturated dicarboxylic acid and vinyl compound, interpolymers of styrene and acrylic esters, and styrene/isoprene copolymers.

Corrosion inhibitors, also known as anti-corrosive agents, reduce the degradation of the metallic parts contacted by the lubricating oil composition. Illustrative of corrosion inhibitors are phosphosulphurized hydrocarbons and the products obtained by reaction of a phosphosulphurized hydrocarbon with an alkaline earth metal oxide or hydroxide, preferably in the presence of an alkylated phenol or of an alkylphenol thioester, and also preferably in the presence of carbon dioxide. Phosphosulphurized hydrocarbons are prepared by reacting a suitable hydrocarbon such as terpene, a heavy petroleum fraction of a $C_2$ to $C_6$ olefin polymer such a polyisobutylene, with from 5 to 30 wt. % of a sulfie of phosphorus for ½ to 15 hours, at a temperature in the range of 150° C. to 600° F. Neutralization of the phosphosulphurized hydrocarbon may be effected in the manner taught in U.S. Pat. No. 1,969,324.

Oxidation inhibitors reduce the tendency of mineral oils to deteriorate in service which deterioration can be evidenced by the products of oxidation such as sludge and varnish-like deposits on the metal surfaces and by viscosity growth. Such oxidation inhibitors include ZDDP's, aromatic amines such as alkylated diphenyl-amines and phenyl alpha naphthylamine, hindered phenols, copper compounds, alkaline earth metal salts of alkylphenolthioesters having preferably $C_5$ to $C_{12}$ alkyl side chains, eg, calcium nonylphenol sulphide, barium t-octylphenyl sulphide, dioctylphenyl-amine, phenylalphanaphthylamine, phosphosulphurized or sulphurized hydrocarbons, etc.

Friction modifiers serve to impart the proper friction characteristics to lubricating oil compositions such as automatic transmission fluids.

Representative examples of suitable friction modifiers are found in U.S. Pat. No. 3,933,659 which discloses fatty acid esters and amides; U.S. Pat. No. 4,176,074 which describes molybdenum complexes of polyisobutenyl succinic anhydride-amino alkanols; U.S. Pat. No. 4,105,571 which discloses glycerol esters of dimerized fatty acids; U.S. Pat. No. 3,779,928 which discloses alkane phosphonic acid salts; U.S. Pat. No. 3,778,375 which discloses reaction products of a phosphonate with an oleamide; U.S. Pat. No. 3,852,205 which discloses S-carboxyalkylene hydrocarbyl succinimide, s-carboxyalkylene hydrocarbyl succinamic acid and mixtures thereof; U.S. Pat. No. 3,879,306 which discloses N-(hydroxyalkyl)alkenyl-succinamic acids or succinimides; U.S. Pat. No. 3,932,290 which discloses reaction products of di-(lower alkyl) phosphites and epoxides; and U.S. Pat. No. 4,028,258 which discloses the alkylene oxide adduct of phosphosulphurized N-(hydroxyalkyl) alkenyl succinimides. The most preferred friction modifiers are succinate esters, or metal salts thereof, of hydrocarbyl substituted succinic acids or anhydrides and thiobis alkanols such as described in U.S. Pat. No. 4,344,853.

Dispersants maintain oil insolubles, resulting from oxidation during use, in suspension in the fluid thus preventing sludge flocculation and precipitation or deposition on metal parts. Suitable dispersants include high molecular weight alkenyl succinimides, the reaction product of oil-soluble polyisobutylene succinic anhydride with ethylene amines such as tetraethylene pentamine and borated salts thereof.

Pour point depressants lower the temperature at which the fluid will flow or can be poured. Such depressants are well known. Typically of those additives which usefully optimize the low temperature fluidity of the fluid are $C_8$–$C_{18}$ dialkylfumarate vinyl acetate copolymers, polymethacrylates, and wax naphthalene. Foam control can be provided by an antifoamant of the polysiloxane type, eg, silicone oil and polydimethyl siloxane.

Detergents and metal rust inhibitors include the metal salts of sulphonic acids, alkyl phenols, sulphurized alkyl phenols, alkyl saliscylates, naphthenates and other oil soluble mono- and di-carboxylic acids.

Highly basic (viz, overbased) metals salts, such as highly basic alkaline earth metal sulphonates (especially Ca and Mg salts) are frequently used as detergents.

Copper and lead corrosion inhibitors and antiwear agents include borate esters, thiadiazoles such as derivatives of 2, 5 dimercapto 1,3,4-thiadiazole and benzotriazoles.

Some of these numerous additives can provide a multiplicity of effects, eg a dispersant-oxidation inhibitor. This approach is well known and need not be further elaborated herein.

Compositions when containing these conventional additives are typically blended into the base oil in amounts which are effective to provide their normal attendant function. Representative effective amounts of such additives are illustrated as follows:

| Additive | Vol % | Wt % a.i. |
| --- | --- | --- |
| Viscosity Modifier | .01–4 | .01–4 |
| Corrosion Inhibitor | 0.01–1 | .01–1.5 |
| Oxidation inhibitor | 0.01–1 | .01–1.5 |
| Dispersant | 0.1–7 | 0.1–8 |
| Pour Point Depressant | 0.01–1 | .01–1.5 |
| Anti-Foaming Agents | 0.001–0.1 | .001–0.15 |
| Anti-Wear Agents | 0.001–1 | .001–1.5 |
| Friction Modifiers | 0.01–1 | .01–1.5 |
| Detergents/Rust Inhibitors | .01–2.5 | .01–3 |
| Mineral Oil Base | Balance | Balance |

When other additives are employed, it may be desirable, although not necessary, to prepare additive concentrates comprising concentrated solutions or dispersions of the dispersant (in concentrate amounts hereinabove described), together with one orm ore of said other additives (said concentrate when constituting an additive mixture being referred to herein as an additive-package) whereby several additives can be added simultaneously to the base oil to form the lubricating oil composition. Dissolution of the additive concentrate into the lubricating oil may be facilitated by solvents and by mixing accompanied with mild heating, but this is not essential. The concentrate or additive-package will typically be formulated to contain the dispersant additive and optional additional additives in proper amounts to provide the desired concentration in the final formulation when the additive-package is combined with a predetermined amount of base lubricant. Thus, the dispersant of the present invention can be added to small amounts of base oil or other compatible solvents along with other desirable additives to form additive-packages containing active ingredients in collective amounts of typically from about 2.5 to about 90%, and preferably from about 5 to about 75%, and most preferably from about 8 to about 50% by weight additives in the appropriate proportions with the remainder being base oil.

The final formulations may employ typically about 10 wt. % of the additive-package with the remainder being base oil.

All of said weight percents expressed herein are based on active ingredient (a.i.) content of the additive, and/or upon the total weight of any additive-package, or formulation which will be the sum of the a.i. weight of each additive plus the weight of total oil or diluent.

The amount of the mixture of dithiophosphate added to the lubricating oil is a minor proportion by weight, preferably less than 20% by weight, more preferably 0 2 to 2.0 and especially 0.5 to 1.5 % by weight.

Additives for lubricating oils are generally supplied as concentrates in solvent (eg oil) for incorporation into the bulk lubricant. According to this invention a concentrate comprises a solvent and 20 to 90 weight % of the metal dithiophosphate of this invention. Suitable solvents include kerosene, aromatic naphthas, mineral lubricating oils etc. Such concentrates may contain one or more other lubricant additives such as described above to form a package which may be diluted with lubricant basestock to form a lubricating oil cmposition.

EXAMPLE 1

In this Example a zinc dithiophosphate was prepared from a dithiophosphoric acid derived from 2-ethyl hexanol and an alcohol having the formula

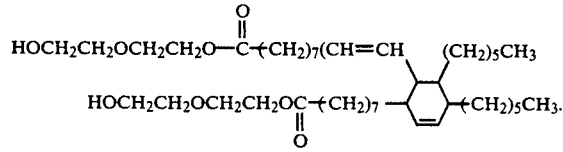

hereinafter referred to as alcohol A.

111 g of phosphorus pentasulphide was added to a mixture of 253 g of 2-ethyl hexanol and 75 g of alcohol A over 2 hours at a temperature of 120° C., followed by a 1 hour heat soak at 85° C. The reaction mixture was cooled and filtered. The resulting dithio phosphoric acid had a content of phosphorus of 7.2 weight %.

To prepare the zinc dithiophosphate with a Zn/P molar ratio of 1:1 a reaction vessel was charged with 90 g of the acid mixture followed by the addition of 34.7 g of ZnO over several minutes. The temperature rose from 22 to 55° C. and after 0.5 hr/50° C. heat soak, the temperature was raised to 80° C. and the rest of the acid (260 g) was added over 2 hours, followed by a 1 hour soak at 85° C.

After stripping and filtration, a clear filtrate was obtained (basic Zn 0.85%) which was soluble in a mineral oil at 1.5% at ambient temperature and at 0° C. This product contained the equivalent of about 16% (wt) of alcohol A. Its analysis was Zn =8.4 wt %, P =8.1 wt % and S =16.7 wt %.

EXAMPLE 2

The product (X) obtained in Example 1 was tested in the four ball friction tests. (1 rpm, 5 kg, 110° C.). The results shown below indicate that X has good friction properties

| Composition | 1 | 2 |
|---|---|---|
| Succinimide dispersant | 4.5 | 4.5 |
| Overbased Mg sulphonate | 1.0 | 1.0 |
| ZDDP (1) | 1.4 | — |
| X | — | 1.5 |
| Mineral Oil | 93.1 | 93.0 |
| μ | 0.24, 0.21 | 0.061 |

(1) zinc bis(2-ethylhexyl) dithiophosphate.

It is seen that composition 2 containing X has much better friction properties than composition 1 which contains a previously known ZDDP.

EXAMPLE 3

A mixture of Plexol 305 (a mixture of polyoxyethylene alkyl phenols having 3 and 4 oxyethylene groups) (102 g) and isooctanol (238 g) was heated to 110° C. and $P_2S_5$ (110 g) added over 2 hours. The dithiophosphoric acid thus obtained was heat soaked for 1 hr/85° C., cooled and filtered. The P content was 7.1 wt %. Part of the acid (100 g) was charged to a reaction pot at ambient temperature and ZnO (34.1g) and zinc acetate (1.0 g) added. The temperature rose to 50° C. and stirring continued for 30 mins. The temperature was increased to 85° C. and a further 250 g of the acid added over 1.5 hours. The ZDDP was heat soaked for 2 hours at 85° C., flocculated, stripped and filtered to give a clear mobile liquid (this analysed as Zn=7.2; P=6.4; S=12.1 wt %) with good oil solubility.

EXAMPLE 4

2-Ethylhexanol (218 g) and glyceryl monoleate heated to 85° C. and $P_2S_5$ (111g) added over 2 hours. The acid was heat soaked for 2 hours, cooled and filtered. The acid was found to contain 7.4 wt % P. 100 g of the acid was charged to a reaction pot and 30 g ZnO plus 0.8 g zinc acetate were added. The temperature rose to 4° C., and the mixture was heat soaked for 30 mins. at 0° C. The temperature was then raised to 50° C. and a further 200 g of the dithiophosphoric acid added over 1 hour. The ZDDP thus obtained was heat soaked for 2 hours at 85° C., flocculated, stripped and filtered to give a clear mcbile liquid oil-soluble product containing Zn 7.9; P 7.3; S 13.1 wt %.

EXAMPLE 5

Storage Stability Tests

These were carried out on fully formulated oil containing dispersant, detergent on V.I. improver, the only difference being in one case a conventional $C_8$ ZDDP and friction modififer A (alcohol A of Example 1) was used whereas in the other case the new ZDDP with built-in friction modifier (product X of Example 1) used:

|  | 1 |  | 2 |  |
|---|---|---|---|---|
| $C_8$ZDDP | 1.3 wt % | Modified $C_8$ ZDDP | 1.4% | |
| Friction modifier A | 0.10 wt % | (product X) | | |
| Storage Stability | | | | |
| 25° C. | 60° C. | 25° C. | | 60° C. |
| Hazy (3 days) | 13% flocculated (3 days) | | | |
| 18% flocculated (8 days) | 9% flocculated (8 days) | clear and bright (8 days) | | |

It is noted that the modified $C_8$ ZDDP in 2 effectively provides 0.5% of friction modifier A, yet still had much better storage stability. It is not possible to dissolve more than 0.1% friction modifier A itself into a blend because of solubility problems.

EXAMPLE 6

Wear Testing

Wear tests were carried out using a reciprocating piston liner section running on a fixed piston ring section at a load of 120 kg for 2 hours. Lower rates of wear were obtained for the two friction modified ZDDPs. The same fully formulated oil, apart from the ZDDP, was used in all cases, and the ZDDPs were compared at 0.1% P treat.

|  | Wear μm | |
|---|---|---|
|  | 1 hour | 2 hours |
| $C_8$ ZDDP | 3.2 | 2.0 |
| $C_8$ ZDDP modified with A (Product X of Example 1) | 2.2 | 1.1 |
| $C_4/C_5$ ZDDP | 10.6 | 2.2 |
| $C_4/C_5$ ZDDP modified with A (Contained the equivalent of about 21 wt % of A) | 3.1 | 1.4 |

What is claimed is:

1. A metal dithiophosphate comprising reaction product of basic compound selected from the group consisting of zinc compounds, copper compounds and molybdenum compounds with dithiophosphoric acid, said dithiophosphoric acid comprising reaction product of phosphorus pentasulphide with mixture of alcohols comprising at least one first alcohol represented by the formula ROH wherein R is an aliphatic hydrogen and carbon containing group having at least 4 carbon atoms or alkaryl group, and at least one second alcohol selected from the group consisting of (i) at least one alcohol represented by the formula:

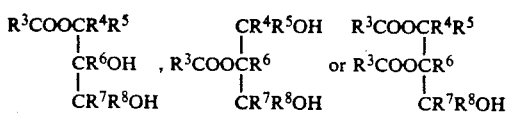

wherein $R^3$ is an aliphatic hydrogen and carbon containing group containing at least 9 carbon atoms and $R^4$, $R^5$, $R^6$ and $R^7$ are independently hydrogen or alkyl groups, and at least one alcohol represented by the formula $R^1(OH)_m$ wherein m is 1 or 2 and $R^1$ comprises hydrogen and carbon containing group containing at least 12 carbon atoms and containing (a)

group or (b) group represented by the formula $+(C_nH_{2n-p}R^2_pO)_q$ wherein $R^2$ is alkylene group, n is an integer of from 2 to 5, p is zero or an integer of from 1 to 5, and q is an integer of 2 or more, with the proviso that p is less than 2n.

2. A dithiophosphate according to claim 1 wherein R is 2-ethyl hexyl.

3. A dithiophosphate according to claim 1, wherein $R^1(OH)_m$ is an oxazoline of the formula

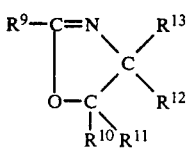

where $R^0$ is alkyl or alkenyl, $R^{10}$ and $R^{11}$ are hydrogen or alkyl and $R^{12}$ and $R^{13}$ are alkyl or hydroxy alkyl provided at least one of them is hydroxy alkyl.

4. A dithiophosphate according to claim 3 wherein $R^1(OH)_m$ is

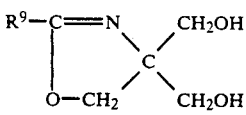

5. A dithiophosphate according to claim 1 wherein $R^1(OH)_m$ is alcohol represented by the formula

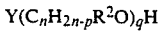

wherein Y is selected from the group consisting of

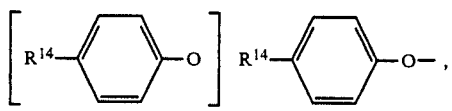

$R^{14}COO-$ or $R^{14}CH_2O-$ wherein $R^{14}$ is an aliphatic hydrocarbon radical having at least 4 carbon atoms.

6. A dithiophosphate according to claim 5 wherein $R^1$ is represented by the formula

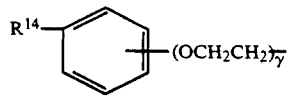

wh3re $R^{14}$ is $C_8$ or $C_9$ alkyl and γ is 3 or 4.

7. A dithiophosphate according to claim 1, wherein $R^1(OH)_m$ is a hydroxy ester derived from the esterfication of a polycarboxylic acid with a polyglycol.

8. A dithiophosphate according to claim 7 wherein $R^1(OH)_m$ is a hydroxy ester of the formula

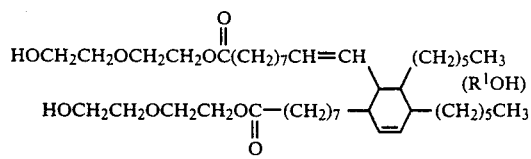

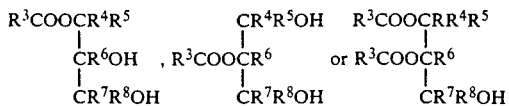

9. A dithiophosphate according to claim 1 wherein $R^1(OH)_m$ is glyceryl mono oleate.

10. A dithiophosphate selected from the group consisting of:

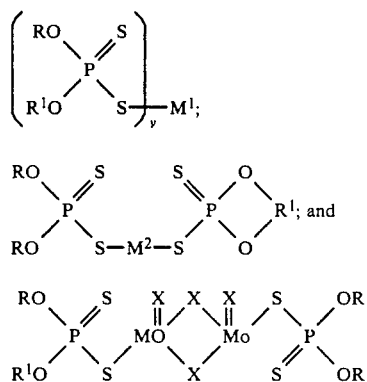

where $M^1$ is cuprous or cupric copper or zinc, $M^2$ is cupric copper or zinc, v is the valency of the metal, X is S or O, R is an aliphatic hydrogen and carbon containing group having at least 4 carbon atoms or alkaryl group, and $R^1$ comprises hydrogen and carbon containing group containing at least 12 carbon atoms and containing (a)

group or (b) group represented by the formula $+C_nH_{2n-p}R^2{}_pO)_q$ wherein $R^2$ is alkylene group, n is an integer of from 2 to 5, p is zero or an integer of from 1 to 5, and q is an integer of 2 or more, with the proviso that p is less than 2n.

11. A lubricating oil composition comprising lubricating oil and a minor proportion by weight of a metal dithiophosphate comprising reaction product of basic compound selected from the group consisting of zinc compounds, copper compounds and molybdenum compounds with dithiophosphoric acid, said dithiophosphoric acid comprising reaction product of phosphorus pentasulphide with mixture of alcohols comprising at least one first alcohol represented by the formula ROH wherein R is an aliphatic hydrogen and carbon containing group having at least 4 carbon atoms or alkaryl group, and at least oen second alcohol selected from the group consisting of (i) at least one alcohol represented by the formula $$\begin{array}{ccc} R^3COOCR^4R^5 & CR^4R^5OH & R^3COOCR^4R^5 \\ | & | & | \\ CR^6OH & , R^3COOCR^6 & \text{or } R^3COOCR^6 \\ | & | & | \\ CR^7R^8OH & CR^7R^8OH & CR^7R^8OH \end{array}$$

wherein $R^3$ is an aliphatic hydrogen and carbon containing group containing at least 9 carbon atoms and $R^4$, $R^5$, $R^6$ and $R^7$ are independently hydrogen or alkyl groups, and (ii) at least one alcohol represented by the formula $R^1(OH)_m$ wherein m is 1 or 2 and $R^1$ comprises hydrogen and carbon containing group containing at least 12 carbon atoms and containing (a)

group or (b) group represented by the formula $+C_nH_{2n-p}R^2{}_pO)_q$ wherein $R^2$ is alkylene group, n is an integer of from 2 to 5, p is zero or an integer of from 1 to 5, and q is an integer of 2 or more, with the proviso that p is less than 2n.

12. A composition according to claim 11 wheich contains 0.2 to 2.0 weight % of the dithiophosphate.

13. A concentrate comprising solvent and 20 to 90 weight % of metal dithiophosphate comprising reaction product of basic compound selected from the gorup consisting of zinc compounds, copper compounds and molybdenum compounds with dithiophosphoric acid, said dithiophosphoric acid comprising reaction product of phosphorus pentasulphide with mixture of alcohols comprising at least one first alcohol represented by the formula ROH wherein R is an aliphatic hydrogen and carbon containing group having at least 4 carbon atoms or alkaryl group, and at least one second alcohol selected from the group consisting of (i) at least one alcohol represented by the formula $$\begin{array}{ccc} R^3COOCR^4R^5 & CR^4R^5OH & R^3COOCR^4R^5 \\ | & | & | \\ CR^6OH & , R^3COOCR^6 & \text{or } R^3COOCR^6 \\ | & | & | \\ CR^7R^8OH & CR^7R^8OH & CR^7R^8OH \end{array}$$

wherein $R^3$ is an aliphatic hydrogen and carbon containing group containing at least 9 carbon atoms and $R^4$, $R^5$, $R^6$ and $R^7$ are independently hydrogen or alkyl groups, and at least one alcohol represented by the formula $R^1(OH)_m$ wherein m is 1 or 2 and $R^1$ comprises hydrogen and carbon containing groups containing at least 12 carbon atoms and containing (aZ)

group or (b) group represented by the formula $+C_nH_{2n-p}R^2{}_pO)_q$ wherein $R^2$ is alkylene group, n is an integer of from 2 to 5, p is zero or an integer of from 1 to 5, and q is an integer of 2 or more, with the proviso that p is less than 2n.

* * * * *